United States Patent [19]
Aida et al.

[11] Patent Number: 6,127,309
[45] Date of Patent: *Oct. 3, 2000

[54] CATALYST FOR USE IN THE ALKYLATION OF ISOALKANES

[75] Inventors: Fuyuki Aida; Yoshio Tajima; Mitsuo Matsuno, all of Yokohama, Japan

[73] Assignee: Nippon Oil Co., Ltd., Tokyo, Japan

[*] Notice: This patent issued on a continued prosecution application filed under 37 CFR 1.53(d), and is subject to the twenty year patent term provisions of 35 U.S.C. 154(a)(2).

[21] Appl. No.: 08/929,362

[22] Filed: Sep. 9, 1997

[30] Foreign Application Priority Data

Sep. 19, 1996 [JP] Japan ................................. 8-269278
Apr. 14, 1997 [JP] Japan ................................. 9-111970

[51] Int. Cl.[7] .................... B01J 27/053; B01J 27/049; B01J 27/08
[52] U.S. Cl. .................... 502/217; 502/216; 502/218; 502/221; 502/224; 502/225; 502/227
[58] Field of Search .................... 502/216, 217, 502/218, 221, 224, 225, 227

[56] References Cited

U.S. PATENT DOCUMENTS

| | | | |
|---|---|---|---|
| 3,717,586 | 2/1973 | Suggitt et al. | 585/721 |
| 4,044,069 | 8/1977 | Bernard et al. | 260/683.47 |
| 4,045,504 | 8/1977 | Brooke et al. | 260/669 R |
| 4,110,251 | 4/1978 | Lauder et al. | 252/442 |
| 4,197,188 | 4/1980 | Antos | 208/139 |
| 4,363,746 | 12/1982 | Capshew | 252/429 B |
| 4,477,587 | 10/1984 | Band | 502/111 |
| 4,650,778 | 3/1987 | Klabunde et al. | 502/8 |
| 5,082,817 | 1/1992 | Albizzati et al. | 502/102 |
| 5,220,095 | 6/1993 | Hommeltoft et al. | 585/721 |
| 5,332,707 | 7/1994 | Karayannis et al. | 502/113 |
| 5,387,567 | 2/1995 | Tajima et al. | 502/103 |
| 5,451,555 | 9/1995 | Tajima et al. | 502/103 |
| 5,556,821 | 9/1996 | Aida et al. | 502/113 |
| 5,574,201 | 11/1996 | Kallenbach | 585/730 |

FOREIGN PATENT DOCUMENTS

WO 94/10106  5/1994  WIPO.

OTHER PUBLICATIONS

Application Ser. No. 08/887,764, Tajima et al., filed 7/3/;97.

*Primary Examiner*—Elizabeth D. Wood
*Attorney, Agent, or Firm*—Akin, Gump, Strauss,, Hauer & Feld, L.L.P.

[57] ABSTRACT

A catalyst useful for the alkylation of isoalkanes is disclosed along with a process therefor the same. The catalyst comprises a zirconium halide and at least one member of the group consisting of sulfate basic sulfate, copper halide, copper nitrate and copper salt of an organic acid. The process for the alkylation of isoalkanes with alkenes is carried out in the presence of a catalyst comprising a zirconium halide and at least one member of the group consisting of sulfate, basic sulfate, copper halide, copper nitrate and copper salt of an organic acid at a temperature of room temperature—200° C. and a pressure of atmospheric –5 MPa.

11 Claims, No Drawings

CATALYST FOR USE IN THE ALKYLATION OF ISOALKANES

BACKGROUND OF THE INVENTION

1. Field of the Invention

This invention relates to the alkylation of isoalkanes and catalysts therefor.

2. Prior Art

In line with the global move for environmental protection, there has been considerable improvement in gasoline materials for automotive fuels which are relatively free of environmentally harmful alkenes and aromatics. A notable example of such improved gasoline material is an alkylate rich in highly branched alkane contents. Such alkylates may be derived by reacting an isoalkane with an alkene of 3–6 carbon atoms. This reaction is usually accompanied by objectionable side reactions such as isomerization, polymerization, cracking, disproportionation and so on. To eliminate or suppress these side reactions, it has been proposed to use an alkylation catalyst which comprises a relatively strong acid such as typically sulfuric acid and hydrofluoric acid. However, sulfuric acid is highly corrosive, leading to increased energy required for removal of reaction heat. Hydrofluoric acid is difficult or tedious to handle. These highly acidic catalysts have been replaced by a solid acid catalyst such as zeolite, $BF_3$ modified zeolite, Lewis acid and/or Brönsted acid supported on an inorganic carrier (such as for example $SO_4^{2-}$–$ZrO_2$) and chlorinated alumina. However, such solid acid catalysts have a drawback when used in the alkylation of isoalkanes in that higher molar ratios of for example isobutane/alkane are needed to suppress objectionable side reactions, and another drawback in that unsaturated oligomers tend to deposit on the acid site of the catalyst to cause quick catalytic deterioration, resulting in frequent catalyst reactivation. Whereas, the use of such a zeolite as comprising a relatively weak solid acid would involve extremely high reaction temperature.

WO94/10106 discloses reacting alkenes with isoalkanes to produce alkylates in the presence of a catalyst comprising an organosulfonic acid having at least one C—F or C—P bond and a Lewis acid. The disclosed process is still disadvantageous because of the use of boron trifluoride ($BF_3$) which is highly toxic and corrosive, hence demanding extreme caution in handling the catalyst.

BRIEF SUMMARY OF THE INVENTION

With the foregoing drawbacks of the prior art in view, the present invention seeks to provide such a catalyst useful in the alkylation of isoalkanes which is easy to make and handle, energy-efficient and least susceptible to heavy side-products.

The invention also seeks to provide an alkylation process in which isoalkanes are reacted with alkenes in the presence of the above catalyst to provide increased rate of alkene conversion and higher yield of highly branched isoalkanes.

According to one aspect of the invention there is provided a catalyst for use in the alkylation of isoalkanes which comprises a zirconium halide and a metal sulfate and/or a basic sulfate.

The invention provides another catalyst for the alkylation of isoalkanes which comprises a zirconium halide and one or more of copper compounds selected from the group consisting of copper halide, copper nitrate and copper salts of organic acids.

According to another aspect of the invention there is provided a process for the alkylation of isoalkanes with alkenes in the presence of either of the above catalysts.

DETAILED DESCRIPTION OF THE INVENTION

The term zirconium halide, or component (A), as used herein preferably includes zirconium tetrahalide such as zirconium tetrachloride, zirconium tetrabromide and zirconium tetraiodide, of which zirconium tetrachloride is particularly preferred.

The term sulfate referred to herein embraces both normal salt and hydrogen salt (acid salt). The term metals associated with these salts as used herein includes sodium, potassium, magnesium, calcium, titanium, zirconium, chromium, tungsten, manganese, iron, cobalt, nickel, copper, zinc and aluminum and the term metal sulfate, or component (B), as used herein specifically includes sodium sulfate [$Na_2SO_4$], sodium hydrogen sulfate [$NaHSO_4$], potassium sulfate [$K_2SO_4$], potassium hydrogen sulfate [$KHSO_4$], magnesium sulfate [$MgSO_4$], calcium sulfate [$CaSO_4$], titanium sulfate [$Ti(SO_4)_2$], zirconium sulfate [$Zr(SO_4)_2$], chromium sulfate [$Cr_2(SO_4)_3$], manganese sulfate [$MnSO_4$], iron sulfate [$FeSO_4$ and $Fe_2(SO_4)_3$], cobalt sulfate [$CoSO_4$], nickel sulfate [$NiSO_4$], copper sulfate [$Cu_2SO_4$ and $CuSO_4$], zinc sulfate [$ZnSO_4$] and aluminum sulfate [$Al_2(SO_4)_3$], particularly preferred among which are copper sulfates and iron sulfates.

The term basic sulfate, or an alternative component (B), as used herein designates salts of iron, titanium and cobalt, of which iron and titanium salts are particularly preferred. The term basic iron sulfate includes $2Fe_2O_3 \cdot 5SO_3$, $Fe_2O_3 \cdot 2SO_3$, $2Fe_2O_3 \cdot 3SO_3$, $3Fe_2O_3 \cdot 4SO_3$, $Fe_2O_3 \cdot SO_3$ and $2Fe_2O_3 \cdot SO_3$, of which $Fe_2O_3 \cdot 2SO_3$ is particularly preferred. The term basic titanium sulfate includes $TiO_2 \cdot SO_3$.

The above sulfates and basic sulfates may be anhydrous or may contain crystallization water, adsorption water and structural water. In the case of the sulfates, however, these should preferably be anhydrous. If the catalyst contains water, this may be heat-treated to remove part or all of the water in the air or in a hydrogen or nitrogen atmosphere at about 100–1,000° C. In the case of copper sulfate [$CuSO_4 \cdot 5H_2O$], 2 molecules of water, 4 molecules of water and 5 molecules of water are removed at 45° C., 110° C. and 250° C., respectively. The treating temperature should not exceed 600°, lest the sulfate should turn into copper oxide. Iron sulfate [$FeSO_4 \cdot 7H_2O$] loses 3 molecules of water, 3 molecules of water and 6 molecules of water at 20°–73° C., 80°–73° C. and 800°–123° C., respectively, and tends to convert into basic iron sulfate at a temperature above 156° C., or become anhydrous when heated to 300° C. in a hydrogen atmosphere.

There may be added other suitable catalyst components such as for example halogen-containing magnesium compound (except sulfates) such as a magnesium halide or a magnesium oxyhalide. The magnesium halide includes magnesium chloride ($MgCl_2$), magnesium bromide ($MgBr_2$) and magnesium iodide ($MgI_2$), of which magnesium chloride is particularly preferred. These magnesium halides may be anhydrous or hydrates of 2, 4, 6, 8 and 12 which are preferably calcined (prior to copulverization) at 150°–300° C. for 1–15 hours usually in the air or in nitrogen gas. The magnesium oxyhalide which may be represented by Mg(OH)X wherein X is halogen, or a sintered product of a compound of the formula $aMgO \cdot bMgX_2 \cdot cH_2O$ wherein X is halogen and a, b and c each are an integer. The Mg(OH)X compound includes magnesium oxychloride [Mg(OH)Cl], magnesium oxybromide [Mg(OH)Br] and magnesium oxyiodide [Mg(OH)I]. Magnesium oxychloride [Mg(OH)Cl] may be obtained by calcination $MgCl_2 \cdot 6H_2O$ at 250°

C.–300° C. for about 1–15 hours. The aMgO·bMgX$_2$·cH$_2$O compound where X is chlorine typically includes 5MgO·MgCl$_2$·13H$_2$O, 10MgO·MgCl$_2$·18H$_2$O, MgO·MgCl$_2$·H$_2$O[Mg(OH)Cl], and MgO·MgCl$_2$·6H$_2$O. These are preferably calcined in the air or in nitrogen atmosphere usually at 150°–300° C. for about 1–15 hours prior to blending with the inventive catalysts.

The above additional catalyst component (B), though not restrictively, is added in an amount of generally less than 1,000 mols, preferably 0.001–500 mols, more preferably 0.01–100 mols, most preferably 0.1–50 mols per mol of catalyst component (A). Other catalyst components such as exemplified above may be added in an amount of 0.001–1, 000, preferably 0.01–100 times the sum of components (A) and (B).

The catalyst components (A) and (B) may be fed to the alkylation reaction system separately or after they are mixed together in advance as in the following manner and sequence.

i) Components (A) and (B) and other components are simultaneously mixed together.

ii) Components (A) and (B) are first mixed and then with other components.

iii) Component (B) and other components are mixed and thereafter with component (A).

iv) Component (A) and other components are mixed together and thereafter with component (B).

Whether other components are used or not, the mixing may be effected in a paraffinic hydrocarbon solvent such as hexane and heptane substantially unreactive with the starting compounds at a temperature of 0° C.-solvent boiling point for about 15 minutes to 5 hours with or without stirring, or copulverizing catalyst components in a mixed state importantly in the absence of oxygen and water, preferably in an inert gas atmosphere such as of nitrogen, argon and the like.

There may be used a jet-mill, vibration ball mill, rotary ball mill, disc vibration mill, rod mill, impulse mill or stirrer for the pulverization of the starting compounds which may be carried out at –10° C.–200° C., preferably 10° C.–50° C., for about 30 minutes or longer, preferably 3–24 hours, more preferably 10–16 hours. This pulverization is intended to mechanically provide the starting compounds with new surfaces, but with no particular restriction upon the particle size of the resultant pulverized product. However, when the catalyst is to be used in particulate form, its average particle size is preferably 10–200 μm, or 0.5 mm–5 mm when admixed with a binder such as silica, silica·alumina or zeolite.

Granulation of the catalyst may be made for example by kneading the particulate product with alumina or silica sol binder in an inert solvent such as a C$_4$–C$_{10}$ saturated aliphatic hydrocarbon including isobutane, butane, pentane, hexane, heptane, octane, nonane and decane at –20°–50° C. in nitrogen atmosphere for 10 minutes to 5 hours, followed by extrusion. The extrudate may be dried, calcined if necessary, but may be otherwise charged without being dried into the alkylation reaction system.

According to the invention, there is provided a catalyst component (C) in place of component (B) for combined use with catalyst component (A). The component (C) is one or more copper compounds selected from copper halide, copper nitrate and copper salts of organic acids, which copper compounds may be cuprous or cupric. Halogens in the copper halide may be chlorine, bromine and iodine. The salts of organic acids include various carboxylates. These copper compounds may contain crystallization water or may be anhydrous.

The catalyst component (C) specifically includes copper (I) chloride, copper (II) chloride, dihydrous copper (II) chloride, copper (I) bromide, copper (II) bromide, copper (I) iodide, copper (II) iodide, copper (I) nitrate, copper (II) nitrate, trihydrous copper (II) nitrate, hexahydrous copper (II) nitrate, copper (I) acetate, copper (II) acetate, copper (II) formate, copper (II) benzoate, hydrous copper (II) formate and hydrous copper (II) benzoate, of which anhydrous copper halide is preferred and anhydrous cuprous and cupric chlorides are more preferred.

The various copper compounds used in the invention may be anhydrous and preferably free of crystallization water. Those containing crystallization water may be used per se but preferably after calcination to an extent not to decompose the compound. Two or more of different copper compounds may be used in combination.

The catalyst component (C) may be used in an amount of less than 50 mols, preferably 0.001–50 mols, more preferably 0.01–10 mols, most preferably 0.1–2 mols per mol of the catalyst component (A).

The catalyst components (A) and (C) may be fed to the alkylation reaction system separately or after they are mixed together in advance as in the following manner and sequence.

i) the reaction system is fed first with component (A) and then component (C).

ii) The reaction system is fed first with component (C) and then component (A).

iii) Components (A) and (C) are mixed together and thereafter this admixture is fed to the reaction system.

iv) The reaction system is fed first with part of component (A), then with the whole of component (C) and thereafter with the remainder of component (A).

v) The reaction system is fed first with part of component (C), then with the whole of component (A) and thereafter with the remainder of component (C).

vi) The admixture of iii) is fed in batches to the reaction system. The sequence i) is particularly preferred.

Components (A) and (C) may be admixed as in iii) and vi) at –20° C.–50° C., preferably 0° C.—a temperature below the melting point of the solvent, for 10 minutes to 5 hours in the presence of a C$_4$–C$_{10}$ paraffinic hydrocarbon solvent such as hexane and heptane.

The alkylation of isoalkanes according to the invention is carried out in the presence of any or either of the foregoing catalysts, in which instance alkenes are used as the alkylation agent. Eligible alkenes are of 3–6 carbon atoms, including propylene, butene-1, trans-butene-2, cis-butene-2, isobutylene, pentene-1, pentene-2, 2-methylbutene-1, 2-methylbutene-2, hexene-1, hexene-2, 2,3-dimethylbutene, 2-methylpentene-1, and 4-methylpentene-1, of which butene-1, trans-butene-2, cis-butene-2 and isobutylene are particularly preferred. Two or more of these alkenes may be used in combination.

The isoalkanes to be alkylated according to the invention are of 4–6, preferably 4–5 carbon atoms, including isobutane, isopentane and isohexane, of which isobutane is particularly preferred. These isoalkanes may be likewise used in any suitable combination.

Either of the co-reactant isoalkanes and alkenes may not necessarily be of high purity but should usually be 50%, preferably 60% in purity, and may contain other hydrocarbons or hydrogen. Their suitable source of supply is found at the site of hydrocarbon contact cracking.

The mole ratio of alkene:isoalkane in the alkylation system is usually in the range of 1:1–1:1,000, preferably 1:2–1:500, more preferably 1:2–1:50. The alkylation reaction is effected usually at a temperature of room temperature—200° C., preferably 20°–150° C., more preferably 20°–125° C., further preferably 50°–100° C., and at a pressure of atmospheric—5 MPa, preferably 0.3–2 MPa.

The alkylation process may be conducted in either liquid phase or gas phase, but preferably in liquid phase, and in either batch or continuous mode of operation. In the batch operation, the sum of alkene and isoalkane is usually in the range of 1–200 grams, preferably 5–100 grams per gram of the copulverized catalyst, although this may be further variable. Each batch operation may be effected usually for 5 minutes to 5 hours, preferably 10 minutes to 3 hours to complete the reaction.

The continuous mode of alkylation reaction according to the invention is usually conducted by supplying a feedstock (containing co-reactant isoalkane and alkene) through a catalyst bed at a liquid space velocity (LSV) of 0.01–30 h$^{-1}$, preferably 0.1–20 h$^{-1}$.

There may be used water or some lower alcohol such as methanol in the alkylation reaction system so as to provide increased alkene conversion and higher yield of branched isoalkanes, but their addition should be in the range of 0.01–1.2 mols, preferably 0.1–1 mol per gram atom of zirconium.

The alkylation product may be removed for example by means of distillation of unreacted materials which may be recycled to the reaction system if desired.

Alkylation of an isoalkane with an alkene according to the invention will yield highly branched isoalkanes; for instance, reacting an isobutane with butenes will result in increased yield of trimethyl pentane and other materials useful for high octane-number gasoline.

The invention will be further described by way of the following examples which are provided for illustrative purposes but not in a limiting sense.

EXAMPLE 1
Preparation of Catalyst

Cuprous sulfate pentahydrate was dehydrated in nitrogen atmosphere at 400° C. for 3 hours. 12.2 grams of the resulting anhydrous cupric sulfate and 9.5 grams zirconium tetrachloride were charged into a 400 ml stainless steel pot containing 12 pieces of ½ inch stainless steel balls and 4 pieces of 1 inch stainless steel balls in nitrogen atmosphere. The admixture was subjected to copulverization for 16 hours thereby obtaining a catalyst.

Alkylation of Isobutane/Butene-2

There was used a 300 ml autoclave equipped with an electromagnetic induction type stirrer. This autoclave was charged in nitrogen atmosphere with 2.5 grams of the above catalyst, and the reaction system was cooled to −20° C., followed by charging 150 grams isobutane which had been dehydrated by Molecular Sieve 4A and also 8 grams butene-2. The alkylation reaction was allowed to continue at a pressure of 620 kPa after heating the system to 50° C. and thus for 2 hours with stirring. Upon completion of the reaction, the reaction system was cooled and the catalyst was filtered to take out 10 grams product liquid which was then analyzed by gas chromatography to reveal a butene conversion of 125 mass %, a $C_8$ hydrocarbon selection of 50% and a trimethyl pentane selection of 63%. The butene conversion (mass %) was calculated from the ratio of the product (g) to the feed butene (g).

EXAMPLE 2
Alkylation of Isobutane/Butene-2

There was used a 300 ml autoclave equipped with an electromagnetic induction type stirrer. The autoclave was charged in nitrogen atmosphere with 2.5 grams of the catalyst of Example 1, and the reaction system was cooled to −20° C., followed by charging 150 grams isobutane which had been dehydrated by Molecular Sieve 4A and also 8 grams butene-2. The alkylation reaction was allowed to continue at a pressure of 1,000 kPa after heating the system to 70° C. and thus for 2 hours with stirring. Upon completion of the reaction, the reaction system was cooled and the catalyst was filtered to take out 4.0 grams product liquid. This product was then analyzed by gas chromatography to reveal a butene conversion of 50 mass %, a $C_8$ hydrocarbon selection of 45% and a trimethyl pentane selection of 50%.

EXAMPLE 3
Preparation of Catalyst

There was used a 400 ml stainless steel pot containing 12 pieces of ½ inch stainless steel balls and 4 pieces of 1 inch stainless steel balls. Into this pot were charged 12.2 grams anhydrous cupric sulfate and 9.5 grams zirconium tetrachloride in nitrogen atmosphere. The admixture was subjected to copulverization for 16 hours thereby obtaining a catalyst.

Alkylation of Isobutane/Butene-1

There was used a 300 ml autoclave equipped with an electromagnetic induction type stirrer. The autoclave was charged in nitrogen atmosphere with 2.5 grams of the above catalyst, and the reaction system was cooled to −20° C., followed by charging 150 grams isobutane which had been dehydrated by Molecular Sieve 4A and also 8 grams butene-1. The alkylation reaction was allowed to continue at a pressure of 620 kPa after heating the system to 50° C. and thus for 2 hours with stirring. Upon completion of the reaction, the reaction system was cooled and the catalyst was filtered to take out 10 grams product liquid. This product was then analyzed by gas chromatography to reveal a butene conversion of 125 mass %, a $C_8$ hydrocarbon selection of 50% and a trimethyl pentane selection of 60%.

EXAMPLE 4
Preparation of Catalyst

There was used a 400 ml stainless steel pot containing 12 pieces of ½ inch stainless steel balls and 4 pieces of 1 inch stainless steel balls. Into this pot were charged 7.8 grams anhydrous cupric sulfate and 10.8 grams zirconium tetrabromide in nitrogen atmosphere. The admixture was subjected to copulverization for 16 hours thereby obtaining a catalyst.

Alkylation of Isobutane/Butene-2

There was used a 300 ml autoclave equipped with an electromagnetic induction type stirrer. The autoclave was charged in nitrogen atmosphere with 3.0 grams of the above catalyst, and the reaction system was cooled to −20° C., followed by charging 150 grams isobutane which had been dehydrated by Molecular Sieve 4A and also 4 grams butene-2. The alkylation reaction was allowed to continue at a pressure of 620 kPa after heating the system to 50° C. and thus for 2 hours with stirring. Upon completion of the reaction, the reaction system was cooled and the catalyst was filtered to take out 3.5 grams product liquid. This product was then analyzed by gas chromatography to reveal a butene conversion of 88 mass %, a $C_8$ hydrocarbon selection of 30% and a trimethyl pentane selection of 25%.

EXAMPLE 5
Preparation of Catalyst

There was used a 400 ml stainless steel pot containing 12 pieces of ½ inch stainless steel balls and 4 pieces of 1 inch stainless steel balls. Into this pot were charged 10.0 grams anhydrous aluminum sulfate and 10.8 grams zirconium tetrachloride in nitrogen atmosphere. The admixture was subjected to copulverization for 16 hours thereby obtaining a catalyst.

Alkylation of Isobutane/Butene-2

There was used a 300 ml autoclave equipped with an electromagnetic induction type stirrer. The autoclave was charged in nitrogen atmosphere with 2.5 grams of the above catalyst, and the reaction system was cooled to −20° C., followed by charging 150 grams isobutane which had been dehydrated by Molecular Sieve 4A and also 8 grams butene-2. The alkylation reaction was allowed to continue at a pressure of 620 kPa after heating the system to 50° C. and thus for 2 hours with stirring. Upon completion of the reaction, the reaction system was cooled and the catalyst was filtered to take out 4.0 grams product liquid. This product was then analyzed by gas chromatography to reveal a butene conversion of 50 mass %, a $C_8$ hydrocarbon selection of 38% and a trimethyl pentane selection of 40%.

EXAMPLE 6

Preparation of Catalyst

There was used a 400 ml stainless steel pot containing 12 pieces of ½ inch stainless steel balls and 4 pieces of 1 inch stainless steel balls. Into this pot were charged 7.8 grams anhydrous iron (II) sulfate and 4.3 grams zirconium tetrachloride in nitrogen atmosphere. The admixture was subjected to copulverization for 16 hours thereby obtaining a catalyst.

Alkylation of Isobutane/Butene-2

There was used a 300 ml autoclave equipped with an electromagnetic induction type stirrer. The autoclave was charged in nitrogen atmosphere with 2.5 grams of the above catalyst, and the reaction system was cooled to −20° C., followed by charging 150 grams isobutane which had been dehydrated by Molecular Sieve 4A and also 8 grams butene-2. The alkylation reaction was allowed to continue at a pressure of 620 kPa after heating the system to 50° C. and thus for 2 hours with stirring. Upon completion of the reaction, the reaction system was cooled and the catalyst was filtered to take out 6.0 grams product liquid. This product was then analyzed by gas chromatography to reveal a butene conversion of 75 mass %, a $C_8$ hydrocarbon selection of 40% and a trimethyl pentane selection of 41%.

EXAMPLE 7

Preparation of Catalyst

There was used a 400 ml stainless steel pot containing 12 pieces of ½ inch stainless steel balls and 4 pieces of 1 inch stainless steel balls. Into this pot were charged 7.8 grams anhydrous iron (III) sulfate and 4.3 grams zirconium tetrachloride in nitrogen atmosphere. The admixture was subjected to copulverization for 16 hours thereby obtaining a catalyst.

Alkylation of Isobutane/Butene-2

There was used a 300 ml autoclave equipped with an electromagnetic induction type stirrer. The autoclave was charged in nitrogen atmosphere with 2.5 grams of the above catalyst, and the reaction system was cooled to −20° C., followed by charging 150 grams isobutane which had been dehydrated by Molecular Sieve 4A and also 8 grams butene-2. The alkylation reaction was allowed to continue at a pressure of 620 MPa after heating the system to 50° C. and thus for 2 hours with stirring. Upon completion of the reaction, the reaction system was cooled and the catalyst was filtered to take out 3.0 grams product liquid. This product was then analyzed by gas chromatography to reveal a butene conversion of 38 mass %, a $C_8$ hydrocarbon selection of 33% and a trimethyl pentane selection of 30%.

EXAMPLE 8

Preparation of Catalyst

There was used a 400 ml stainless steel pot containing 12 pieces of ½ inch stainless steel balls and 4 pieces of 1 inch stainless steel balls. Into this pot were charged 7.8 grams anhydrous zinc sulfate and 4.3 grams zirconium tetrachloride in nitrogen atmosphere. The admixture was subjected to copulverization for 16 hours thereby obtaining a catalyst.

Alkylation of Isobutane/Butene-2

There was used a 300 ml autoclave equipped with an electromagnetic induction type stirrer. The autoclave was charged in nitrogen atmosphere with 2.5 grams of the above catalyst, and the reaction system was cooled to −20° C., followed by charging 150 grams isobutane which had been dehydrated by Molecular Sieve 4A and also 8 grams butene-2. The alkylation reaction was allowed to continue at a pressure of 620 kPa after heating the system to 50° C. and thus for 2 hours with stirring. Upon completion of the reaction, the reaction system was cooled and the catalyst was filtered to take out 3.0 grams product liquid. This product was then analyzed by gas chromatography to reveal a butene conversion of 38 mass %, a $C_8$ hydrocarbon selection of 30% and a trimethyl pentane selection of 30%.

EXAMPLE 9

Preparation of Catalyst

Iron (II) sulfate heptahydrate was heated at 110° C. in nitrogen atmosphere for 2 hours to obtain iron (II) sulfate monohydrate. 7.8 grams of the calcined iron sulfate and 4.3 grams zirconium tetrachloride were charged in nitrogen atmosphere into a 400 ml stainless steel pot containing 12 pieces of ½ inch stainless steel balls and 4 pieces of 1 inch stainless steel balls in nitrogen atmosphere. The admixture was subjected to copulverization for 16 hours thereby obtaining a catalyst.

Alkylation of Isobutane/Butene-2

There was used a 300 ml autoclave equipped with an electromagnetic induction type stirrer. The autoclave was charged in nitrogen atmosphere with 2.5 grams of the above catalyst, and the reaction system was cooled to −20° C., followed by charging 150 grams isobutane which had been dehydrated by Molecular Sieve 4A and also 8 grams butene-2. The alkylation reaction was allowed to continue at a pressure of 620 kPa after heating the system to 50° C. and thus for 2 hours with stirring. Upon completion of the reaction, the reaction system was cooled and the catalyst was filtered to take out 7.5 grams product liquid. This product was then analyzed by gas chromatography to reveal a butene conversion of 94 mass %, a $C_8$ hydrocarbon selection of 50% and a trimethyl pentane selection of 70%.

EXAMPLE 10

Preparation of Catalyst

Iron (II) sulfate heptahydrate was heated at 300° C. for 2 hours with circulating air to obtain basic iron sulfate. 7.8 grams of the resulting basic iron sulfate and 4.3 grams zirconium tetrachloride were charged into a 400 ml stainless steel pot containing 12 pieces of ½ inch stainless steel balls and 4 pieces of 1 inch stainless steel balls in nitrogen atmosphere. The admixture was subjected to copulverization for 16 hours thereby obtaining a catalyst.

Alkylation of Isobutane/Butene-2

There was used a 300 ml autoclave equipped with an electromagnetic induction type stirrer. The autoclave was charged in nitrogen atmosphere with 2.5 grams of the above catalyst, and the reaction system was cooled to −20° C., followed by charging 150 grams isobutane which had been dehydrated by Molecular Sieve 4A and also 8 grams butene- 2. The alkylation reaction was allowed to continue at a pressure of 620 kPa after heating the system to 50° C. and thus for 2 hours with stirring. Upon completion of the reaction, the reaction system was cooled and the catalyst was filtered to take out 8.0 grams product liquid. This product was then analyzed by gas chromatography to reveal a butene conversion of 100 mass %, a $C_8$ hydrocarbon selection of 51% and a trimethyl pentane selection of 78%.

EXAMPLE 11
Preparation of Catalyst

Titanium sulfate n-hydrate was heated at 600° C. for 2 hours with circulating air. 7.8 grams of the above calcined product and 4.3 grams zirconium tetrachloride was charged in nitrogen atmosphere into a 400 ml stainless steel pot containing 12 pieces of ½ inch stainless steel balls and 4 pieces of 1 inch stainless steel balls. The admixture was subjected to copulverization for 16 hours thereby obtaining a catalyst.

Alkylation of Isobutane/Butene-2

There was used a 300 ml autoclave equipped with an electromagnetic induction type stirrer. The autoclave was charged in nitrogen atmosphere with 2.5 grams of the above catalyst, and the reaction system was cooled to −20° C., followed by charging 150 grams isobutane which had been dehydrated by Molecular Sieve 4A and also 8 grams butene-2. The alkylation reaction was allowed to continue at a pressure of 620 kPa after heating the system to 50° C. and thus for 2 hours with stirring. Upon completion of the reaction, the reaction system was cooled and the catalyst was filtered to take out 11 grams product liquid. This product was then analyzed by gas chromatography to reveal a butene conversion of 138 mass %, a $C_8$ hydrocarbon selection of 55% and a trimethyl pentane selection of 82%.

Comparative Example 1
Alkylation of Isobutane/Butene-2

There was used a 300 ml autoclave equipped with an electromagnetic induction type stirrer. The autoclave was charged in nitrogen atmosphere with 2.5 grams of zirconium tetrachloride, and the reaction system was cooled to −20° C., followed by charging 85 grams isobutane which had been dehydrated by Molecular Sieve 4A and also 7 grams butene-2. The alkylation reaction was allowed to continue at a pressure of 620 kPa after heating the system to 50° C. and thus for 2 hours with stirring. Upon completion of the reaction, the reaction system was cooled and the catalyst was filtered to take out 2.1 grams product liquid. This product was then analyzed by gas chromatography to reveal a butene conversion of 30 mass %, a $C_8$ hydrocarbon selection of 16% and a trimethyl pentane selection of 26%.

EXAMPLE 12
Preparation of Catalyst

There was used a 400 ml stainless steel pot containing 12 pieces of ½ inch stainless steel balls and 4 pieces of 1 inch stainless steel balls. Into this pot were charged 8.5 grams anhydrous copper (I) chloride and 10 grams zirconium tetrachloride in nitrogen atmosphere. The admixture was subjected to copulverization for 16 hours thereby obtaining a catalyst.

Alkylation of Isobutane/Butene-2

There was used a 300 ml autoclave equipped with an electromagnetic induction type stirrer. The autoclave was charged in nitrogen atmosphere with 8.1 grams of the above catalyst, and the reaction system was cooled to −20° C., followed by charging 160 grams isobutane which had been dehydrated by Molecular Sieve 4A and also 4 grams butene-2. The alkylation reaction was allowed to continue at a pressure of 0.62 MPa after heating the system to 50° C. and thus for 2 hours with stirring. The reaction system was cooled to take out 2.8 grams product liquid. This product was then analyzed by gas chromatography to reveal a butene conversion of 70 mass %, a $C_8$ hydrocarbon selection of 82% and a trimethyl pentane selection of 91%.

EXAMPLE 13
Preparation of Catalyst

There was used a 400 ml stainless steel pot containing 12 pieces of ½ inch stainless steel balls and 4 pieces of 1 inch stainless steel balls. Into this pot were charged 4.3 grams anhydrous copper (I) chloride and 10 grams zirconium tetrachloride in nitrogen atmosphere. The admixture was subjected to copulverization for 16 hours thereby obtaining a catalyst.

Alkylation of Isobutane/Butene-2

There was used a 300 ml autoclave equipped with an electromagnetic induction type stirrer. The autoclave was charged in nitrogen atmosphere with 3.1 grams of the above catalyst, and the reaction system was cooled to −20° C., followed by charging 120 grams isobutane which had been dehydrated by Molecular Sieve 4A and also 5 grams butene-2. The alkylation reaction was allowed to continue at a pressure of 0.62 MPa after heating the system to 50° C. and thus for 2 hours with stirring. The reaction system was cooled to take out 6.3 grams product liquid. This product was then analyzed by gas chromatography to reveal a butene conversion of 126 mass %, a $C_8$ hydrocarbon selection of 76% and a trimethyl pentane selection of 90%.

EXAMPLE 14
Preparation of Catalyst

There was used a 400 ml stainless steel pot containing 12 pieces of ½ inch stainless steel balls and 4 pieces of 1 inch stainless steel balls. Into this pot were charged 5.8 grams anhydrous copper (II) chloride and 10 grams zirconium tetrachloride in nitrogen atmosphere. The admixture was subjected to copulverization for 16 hours thereby obtaining a catalyst.

Alkylation of Isobutane/Butene-2

There was used a 300 ml autoclave equipped with an electromagnetic induction type stirrer. The autoclave was charged in nitrogen atmosphere with 10.5 grams of the above catalyst, and the reaction system was cooled to −20° C., followed by charging 100 grams isobutane which had been dehydrated by Molecular Sieve 4A and also 3 grams butene-2. The alkylation reaction was allowed to continue at a pressure of 0.62 MPa after heating the system to 50° C. and thus for 2 hours with stirring. The reaction system was cooled to take out 4.5 grams product liquid. This product was then analyzed by gas chromatography to reveal a butene conversion of 150 mass %, a $C_8$ hydrocarbon selection of 60% and a trimethyl pentane selection of 88%.

EXAMPLE 15
Preparation of Catalyst

There was used a 400 ml stainless steel pot containing 12 pieces of ½ inch stainless steel balls and 4 pieces of 1 inch stainless steel balls. Into this pot were charged 3.5 grams anhydrous copper (I) bromide and 10 grams zirconium tetrabromide in nitrogen atmosphere. The admixture was subjected to copulverization for 16 hours thereby obtaining a catalyst.

Alkylation of Isobutane/Butene-2

There was used a 300 ml autoclave equipped with an electromagnetic induction type stirrer. The autoclave was charged in nitrogen atmosphere with 6.2 grams of the above catalyst, and the reaction system was cooled to −20° C., followed by charging 130 grams isobutane which had been dehydrated by Molecular Sieve 4A and also 2 grams of a mixture of buten isomers (buten-1 8 vol %, cis-buten-2 29 vol %, trans-butene-2 64 vol %). The alkylation reaction was allowed to continue at a pressure of 0.62 MPa after heating the system to 50° C. and thus for 2 hours with stirring. The reaction system was cooled to take out 1.9 grams product liquid. This product was then analyzed by gas chromatography to reveal a butene conversion of 95 mass %, a $C_8$ hydrocarbon selection of 56% and a trimethyl pentane selection of 86%.

EXAMPLE 16
Preparation of Catalyst

There was used a 400 ml stainless steel pot containing 12 pieces of ½ inch stainless steel balls and 4 pieces of 1 inch stainless steel balls. Into this pot were charged 2.7 grams anhydrous copper (I) nitrate and 10 grams zirconium tetrachloride in nitrogen atmosphere. The admixture was subjected to copulverization for 16 hours thereby obtaining a catalyst.

Alkylation of Isobutane/Butene-2

There was used a 300 ml autoclave equipped with an electromagnetic induction type stirrer. The autoclave was charged in nitrogen atmosphere with 8.1 grams of the above catalyst, and the reaction system was cooled to −20° C., followed by charging 120 grams isobutane which had been dehydrated by Molecular Sieve 4A and also 5 grams butene-2. The alkylation reaction was allowed to continue at a pressure of 0.62 MPa after heating the system to 50° C. and thus for 2 hours with stirring. The reaction system was cooled to take out 3.1 grams product liquid. This product was then analyzed by gas chromatography to reveal a butene conversion of 62 mass %, a $C_8$ hydrocarbon selection of 62% and a trimethyl pentane selection of 84%.

EXAMPLE 17
Alkylation of Isobutane/Butene-2

There was used a 300 ml autoclave equipped with an electromagnetic induction type stirrer. The autoclave was charged in nitrogen atmosphere with 1.1 grams anhydrous copper (I) chloride and 5 grams zirconium tetrachloride, and the reaction system was cooled to −20° C., followed by charging 120 grams isobutane which had been dehydrated by Molecular Sieve 4A and also 4 grams butene-2. The alkylation reaction was allowed to continue at a pressure of 0.62 MPa after heating the system to 50° C. and thus for 1 hours with stirring. The reaction system was cooled to take out 2.2 grams product liquid. This product was then analyzed by gas chromatography to reveal a butene conversion of 55 mass %, a $C_8$ hydrocarbon selection of 78% and a trimethyl pentane selection of 85%.

EXAMPLE 18
Preparation of Catalyst

There was used a 400 ml stainless steel pot containing 12 pieces of ½ inch stainless steel balls and 4 pieces of 1 inch stainless steel balls. Into this pot were charged 12.7 grams anhydrous copper (I) chloride and 10 grams zirconium tetrachloride in nitrogen atmosphere. The admixture was subjected to copulverization for 16 hours thereby obtaining a catalyst.

Alkylation of Isobutane/Butene-1

There was used a 300 ml autoclave equipped with an electromagnetic induction type stirrer. The autoclave was charged in nitrogen atmosphere with 4.3 grams of the above catalyst, and the reaction system was cooled to −20° C., followed by charging 100 grams isobutane which had been dehydrated by Molecular Sieve 4A and also 5 grams butene-1. The alkylation reaction was allowed to continue at a pressure of 0.62 MPa after heating the system to 50° C. and thus for 2 hours with stirring. The reaction system was cooled to take out 3.3 grams product liquid. This product was then analyzed by gas chromatography to reveal a butene conversion of 66 mass %, a $C_8$ hydrocarbon selection of 64% and a trimethyl pentane selection of 74%.

EXAMPLE 19
Preparation of Catalyst

There was used a 400 ml stainless steel pot containing 12 pieces of ½ inch stainless steel balls and 4 pieces of 1 inch stainless steel balls. Into this pot were charged 2.6 grams copper (I) acetate and 10 grams zirconium tetrachloride in nitrogen atmosphere. The admixture was subjected to copulverization for 16 hours thereby obtaining a catalyst.

Alkylation of Isobutane/Butene-1

There was used a 300 ml autoclave equipped with an electromagnetic induction type stirrer. The autoclave was charged in nitrogen atmosphere with 10.2 grams of the above catalyst, and the reaction system was cooled to −20° C., followed by charging 100 grams isobutane which had been dehydrated by Molecular Sieve 4A and also 3 grams butene-1. The alkylation reaction was allowed to continue at a pressure of 0.62 MPa after heating the system to 50° C. and thus for 2 hours with stirring. The reaction system was cooled to take out 1.4 grams product liquid. This product was then analyzed by gas chromatography to reveal a butene conversion of 47 mass %, a $C_8$ hydrocarbon selection of 69% and a trimethyl pentane selection of 72%.

EXAMPLE 20
Preparation of Catalyst

There was used a 400 ml stainless steel pot containing 12 pieces of ½ inch stainless steel balls and 4 pieces of 1 inch stainless steel balls. Into this pot were charged 0.6 grams copper (I) chloride and 10 grams zirconium tetrabromide in nitrogen atmosphere. The admixture was subjected to copulverization for 16 hours thereby obtaining a catalyst.

Alkylation of Isobutane/Butene-1

There was used a 300 ml autoclave equipped with an electromagnetic induction type stirrer. The autoclave was charged in nitrogen atmosphere with 8.3 grams of the above catalyst, and the reaction system was cooled to −20° C., followed by charging 160 grams isobutane which had been dehydrated by Molecular Sieve 4A and also 4 grams butene-2. The alkylation reaction was allowed to continue at a pressure of 0.62 MPa after heating the system to 50° C. and thus for 2 hours with stirring. The reaction system was cooled to take out 2.0 grams product liquid. This product was then analyzed by gas chromatography to reveal a butene conversion of 50 mass %, a $C_8$ hydrocarbon selection of 68% and a trimethyl pentane selection of 86%.

EXAMPLE 21
Preparation of Catalyst

There was used a 400 ml stainless steel pot containing 12 pieces of ½ inch stainless steel balls and 4 pieces of 1 inch stainless steel balls. Into this pot were charged 5.8 grams anhydrous copper (II) chloride and 10 grams zirconium tetrachloride in nitrogen atmosphere. The admixture was subjected to copulverization for 16 hours and then added with 2.7 grams anhydrous copper nitrate, follow by another 16 hours-copulverization thereby obtaining a catalyst.

Alkylation of Isobutane/Butene-2

There was used a 300 ml autoclave equipped with an electromagnetic induction type stirrer. The autoclave was charged in nitrogen atmosphere with 5.3 grams of the above catalyst, and the reaction system was cooled to −20° C., followed by charging 100 grams isobutane which had been dehydrated by Molecular Sieve 4A and also 3 grams butene-2. The alkylation reaction was allowed to continue at a pressure of 0.64 MPa after heating the system to 50° C. and thus for 2 hours with stirring. The reaction system was cooled to take out 3.6 grams product liquid. This product was then analyzed by gas chromatography to reveal a butene conversion of 120 mass %, a $C_8$ hydrocarbon selection of 63% and a trimethyl pentane selection of 84%.

EXAMPLE 22

Preparation of Catalyst

There was used a 400 ml stainless steel pot containing 12 pieces of ½ inch stainless steel balls and 4 pieces of 1 inch stainless steel balls. Into this pot were charged 10.6 grams anhydrous copper (I) chloride and 5 grams zirconium tetrachloride in nitrogen atmosphere. The admixture was subjected to copulverization for 16 hours thereby obtaining a catalyst.

Alkylation of Isobutane/Butene-2

There was used a 300 ml autoclave equipped with an electromagnetic induction type stirrer. The autoclave was charged in nitrogen atmosphere with 10 grams of the above catalyst, and the reaction system was cooled to −20° C., followed by charging 160 grams isobutane which had been dehydrated by Molecular Sieve 4A and also 4 grams butene-2. The alkylation reaction was allowed to continue at a pressure of 0.62 MPa after heating the system to 50° C. and thus for 2 hours with stirring. The reaction system was cooled to take out 1.6 grams product liquid. This product was then analyzed by gas chromatography to reveal a butene conversion of 40 mass %, a $C_8$ hydrocarbon selection of 80% and a trimethyl pentane selection of 91%.

EXAMPLE 23

Preparation of Catalyst

There was used a 400 ml stainless steel pot containing 12 pieces of ½ inch stainless steel balls and 4 pieces of 1 inch stainless steel balls. Into this pot were charged 21.2 grams anhydrous copper (I) chloride and 5 grams zirconium tetrachloride in nitrogen atmosphere. The admixture was subjected to copulverization for 16 hours thereby obtaining a catalyst.

Alkylation of Isobutane/Butene-2

There was used a 300 ml autoclave equipped with an electromagnetic induction type stirrer. The autoclave was charged in nitrogen atmosphere with 10 grams of the above catalyst, and the reaction system was cooled to −20° C., followed by charging 160 grams isobutane which had been dehydrated by Molecular Sieve 4A and also 5 grams butene-2. The alkylation reaction was allowed to continue at a pressure of 1 MPa after heating the system to 70° C. and thus for 2 hours with stirring. The reaction system was cooled to take out 2.1 grams product liquid. This product was then analyzed by gas chromatography to reveal a butene conversion of 42 mass %, a $C_8$ hydrocarbon selection of 84% and a trimethyl pentane selection of 90%.

EXAMPLE 24

Preparation of Catalyst

Iron (II) sulfate heptahydrate was heated at 300° C. for 2 hours with circulating air to obtain basic iron sulfate. 15 grams of the resulting basic iron sulfate and 4.3 grams zirconium tetrachloride were charged into a 400 ml stainless steel pot containing 12 pieces of ½ inch stainless steel balls and 4 pieces of 1 inch stainless steel balls in nitrogen atmosphere. The admixture was subjected to copulverization for 16 hours thereby obtaining a catalyst.

Alkylation of Isobutane/Butene-2

There was used a 300 ml autoclave equipped with an electromagnetic induction type stirrer. The autoclave was charged in nitrogen atmosphere with 2.5 grams of the above catalyst, and the reaction system was cooled to −20° C., followed by charging 150 grams isobutane which had been dehydrated by Molecular Sieve 4A and also 8 grams butene-2. The alkylation reaction was allowed to continue at a pressure of 620 kPa after heating the system to 50° C. and thus for 2 hours with stirring. Upon completion of the reaction, the reaction system was cooled and the catalyst was filtered to take out 4 grams product liquid. This product was then analyzed by gas chromatography to reveal a butene conversion of 50 mass %, a $C_8$ hydrocarbon selection of 60% and a trimethyl pentane selection of 82%.

EXAMPLE 25

Preparation of Catalyst

Copper (II) sulfate pentahydrate was dehydrated in nitrogen atmosphere at 400° C. for 3 hours. 12.2 grams of the resulting anhydrous cupric sulfate and 4.8 grams zirconium tetrachloride were charged into a 400 ml stainless steel pot containing 12 pieces of ½ inch stainless steel balls and 4 pieces of 1 inch stainless steel balls in nitrogen atmosphere. The admixture was subjected to copulverization for 16 hours thereby obtaining a catalyst.

Alkylation of Isobutane/Butene-2

There was used a 300 ml autoclave equipped with an electromagnetic induction type stirrer. This autoclave was charged in nitrogen atmosphere with 2.5 grams of the above catalyst, and the reaction system was cooled to −20° C., followed by charging 150 grams isobutane which had been dehydrated by Molecular Sieve 4A and also 8 grams butene-2. The alkylation reaction was allowed to continue at a pressure of 620 kPa after heating the system to 50° C. and thus for 2 hours with stirring. Upon completion of the reaction, the reaction system was cooled and the catalyst was filtered to take out 5.2 grams product liquid. This product was then analyzed by gas chromatography to reveal a butene conversion of 65 mass %, a $C_8$ hydrocarbon selection of 55% and a trimethyl pentane selection of 79%.

What is claimed is:

1. A catalyst for use in the alkylation of isoalkanes which comprises a catalytically effective amount of a zirconium halide and a sulfate component which is at least one of a sulfate and a basic sulfate, wherein said sulfate component is present in an amount of less than 1,000 moles per mole of said zirconium halide.

2. A catalyst according to claim 1 in which said sulfate is selected from the group consisting of sodium sulfate [$Na_2SO_4$], sodium hydrogen sulfate [$NaHSO_4$], potassium sulfate [$K_2SO_4$], potassium hydrogen sulfate [$KHSO_4$], magnesium sulfate [$MgSO_4$], calcium sulfate [$CaSO_4$], titanium sulfate [$Ti(SO_4)_2$], zirconium sulfate [$Zr(SO_4)_2$], chromium sulfate [$Cr_2(SO_4)_3$], manganese sulfate [$MnSO_4$], iron sulfate [$FeSO_4$ and $Fe_2(SO_4)_3$], cobalt sulfate [$COSO_4$], nickel sulfate [$NiSO_4$], copper sulfate [$Cu_2SO_4$ and $CuSO_4$], zinc sulfate [$ZnSO_4$] and aluminum sulfate [$Al_2(SO_4)_3$].

3. A catalyst according to claim 1 in which said basic sulfate is selected from the group consisting of iron, titanium and cobalt salts.

4. A catalyst according to claim 3 in which the basic sulfate is an iron salt and said iron salt is selected from the group consisting of $2Fe_2O_3 \cdot 5SO_3$, $Fe_2O_3 \cdot 2SO_3$, $2Fe_2O_3 \cdot 3SO_3$, $3Fe_2O_3 \cdot 4SO_3$, $Fe_2O_3 \cdot SO_3$, and $2Fe_2O_3 \cdot SO_3$.

5. A catalyst according to claim 1 which further comprises a halogen-containing compound selected from a magnesium halide and a magnesium oxyhalide.

6. The catalyst according to claim 1 which has been pulverized and mechanically provided with new surfaces.

7. A catalyst for use in the alkylation of isoalkanes which comprises a catalytically effective amount of a zirconium halide and a copper component which is at least one member of the group consisting of copper halide, copper nitrate, and copper salt of an organic acid, wherein said copper component is present in an amount of less than 50 moles per mole of said zirconium halide.

8. A catalyst according to claim 7 in which said copper halide is selected from the group consisting of copper (I) chloride, copper (II) chloride, dihydrous copper (II) chloride, copper (I) bromide, copper (II) bromide, copper (I) iodide and copper (II) iodide.

9. A catalyst according to claim 7 in which said copper nitrate is selected from the group consisting of copper (I) nitrate, copper (II) nitrate, trihydrous copper (II) nitrate and hexahydrous copper (II) nitrate.

10. A catalyst according to claim 7 in which said copper salt of an organic acid is selected from the group consisting of copper (I) acetate, copper (II) acetate, copper (II) formate, copper (II) benzoate, hydrous copper (II) formate and hydrous copper (II) benzoate.

11. The catalyst according to claim 7 which has been pulverized and mechanically provided with new surfaces.

* * * * *